US00PP27876P3

(12) United States Plant Patent
Steward

(10) Patent No.: US PP27,876 P3
(45) Date of Patent: Apr. 11, 2017

(54) AZALEA PLANT NAMED 'STEWARD'

(50) Latin Name: ***Rhododendron* sp.**
Varietal Denomination: STEWARD

(71) Applicant: The Ohio State University, Columbus, OH (US)

(72) Inventor: Larry G. Steward, North Fort Myers, FL (US)

(73) Assignee: The Ohio State University, Columbus, OH (US)

( * ) Notice: Subject to any disclaimer, the term of this patent is extended or adjusted under 35 U.S.C. 154(b) by 86 days.

(21) Appl. No.: 14/545,146

(22) Filed: Mar. 31, 2015

(65) Prior Publication Data

US 2015/0282409 P1 Oct. 1, 2015

Related U.S. Application Data

(63) Continuation-in-part of application No. 13/068,201, filed on May 5, 2011, now abandoned, and a continuation of application No. 14/092,552, filed on Nov. 27, 2013, now abandoned.

(51) Int. Cl.
*A01H 5/02* (2006.01)

(52) U.S. Cl.
USPC ..... Plt./238

(58) Field of Classification Search
USPC ..... Plt./238
See application file for complete search history.

(56) References Cited

U.S. PATENT DOCUMENTS

PP18,948 P2 * 6/2008 Bergman ..... Plt./238

OTHER PUBLICATIONS

The International Code of Nomenclature for Cultivated Plants (ICNCP) 2010, retrieved on Aug. 16, 2016, retrieved from the Internet at <http://www.ishs.org/sci/icraname.htm> pp. 1-8.*

* cited by examiner

*Primary Examiner* — June Hwu
(74) *Attorney, Agent, or Firm* — Wood Herron & Evans LLP

(57) ABSTRACT

A new and distinct cultivar of Azalea plant named 'STEWARD', characterized by its globe to broad columnar plant form; freely branching habit; terminal truss flower arrangement; pure white hose-in-hose flowers with some yellow-green flecking in the throat of the petals; green-yellow flower buds; and hardiness in USDA zone 6a.

3 Drawing Sheets

Latin name of the genus and species of the plant claimed: *Rhododendron* sp.

Cultivar denomination: 'STEWARD'.

STATEMENT REGARDING FEDERALLY-SPONSORED RESEARCH AND DEVELOPMENT

Not applicable.

BACKGROUND OF THE INVENTION

The present invention relates to a new and distinct cultivar of Azalea, botanically *Rhododendron*, hereinafter referred to as 'STEWARD'. 'STEWARD' is an evergreen greenhouse-forcing type Azalea and may be used for outside landscape planting.

The new Azalea was discovered by the inventor in Charlottesville, Va. in a controlled, landscape planting of 'Delaware Valley White' Azaleas in 1974. The exact parentage of 'STEWARD' is unknown. Compared to plants of the white, single-flowered commercial cultivar 'Delaware Valley White' that is not patented, the new Azalea has white hose-in-hose flowers borne in trusses with some yellow-green flecking in the throat of the petals and green-yellow emerging buds.

Asexual reproduction of the new Azalea by hardwood, semi-hardwood and softwood vegetative cuttings taken in a controlled environment in Charlottesville, Va. since 1975 and in Wooster, Ohio since 1998 have shown that the unique features of this new Azalea are stable and reproduced true to type in successive generations.

SUMMARY OF THE INVENTION

The following traits have been repeatedly observed and are determined to be the most outstanding and distinguishing characteristics of 'STEWARD'. These traits distinguish 'STEWARD' as a new and distinct cultivar:

1. Globe to broad columnar plant form.
2. Freely branching habit.
3. Terminal truss flower arrangement.
4. Pure white hose-in-hose flowers with some yellow-green flecking in the throat of the petals.
5. Green-yellow flower buds.
6. Subtle fruity scent.
7. Hardy in USDA zone 6a.

BRIEF DESCRIPTION OF THE DRAWINGS

The new Azalea is illustrated by the accompanying photographic prints in landscape format which:

1. The photograph on the FIG. 1 displays a view of a typical flowering plant of 'STEWARD'.

Figure 1:
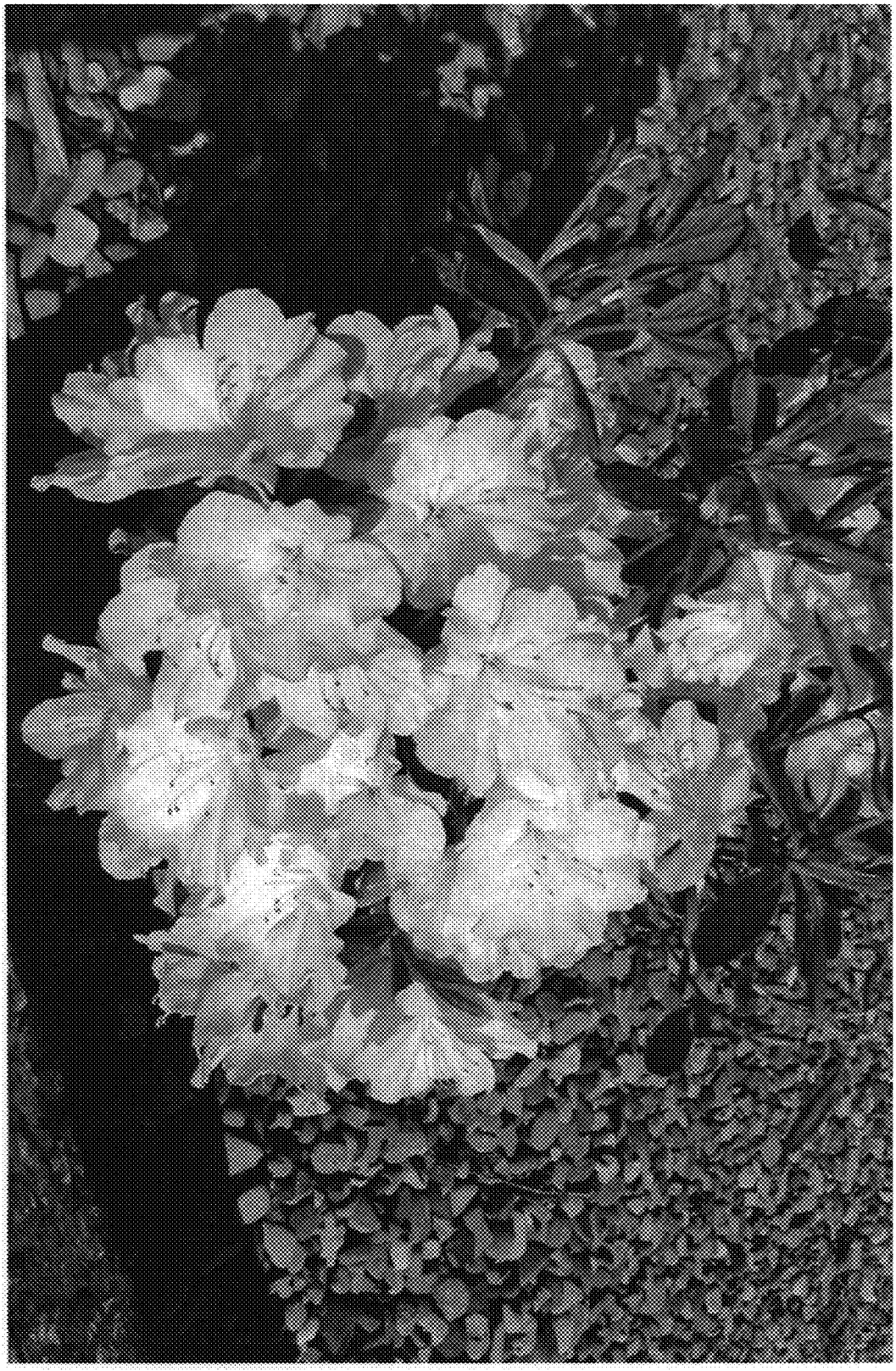
Figure 2:
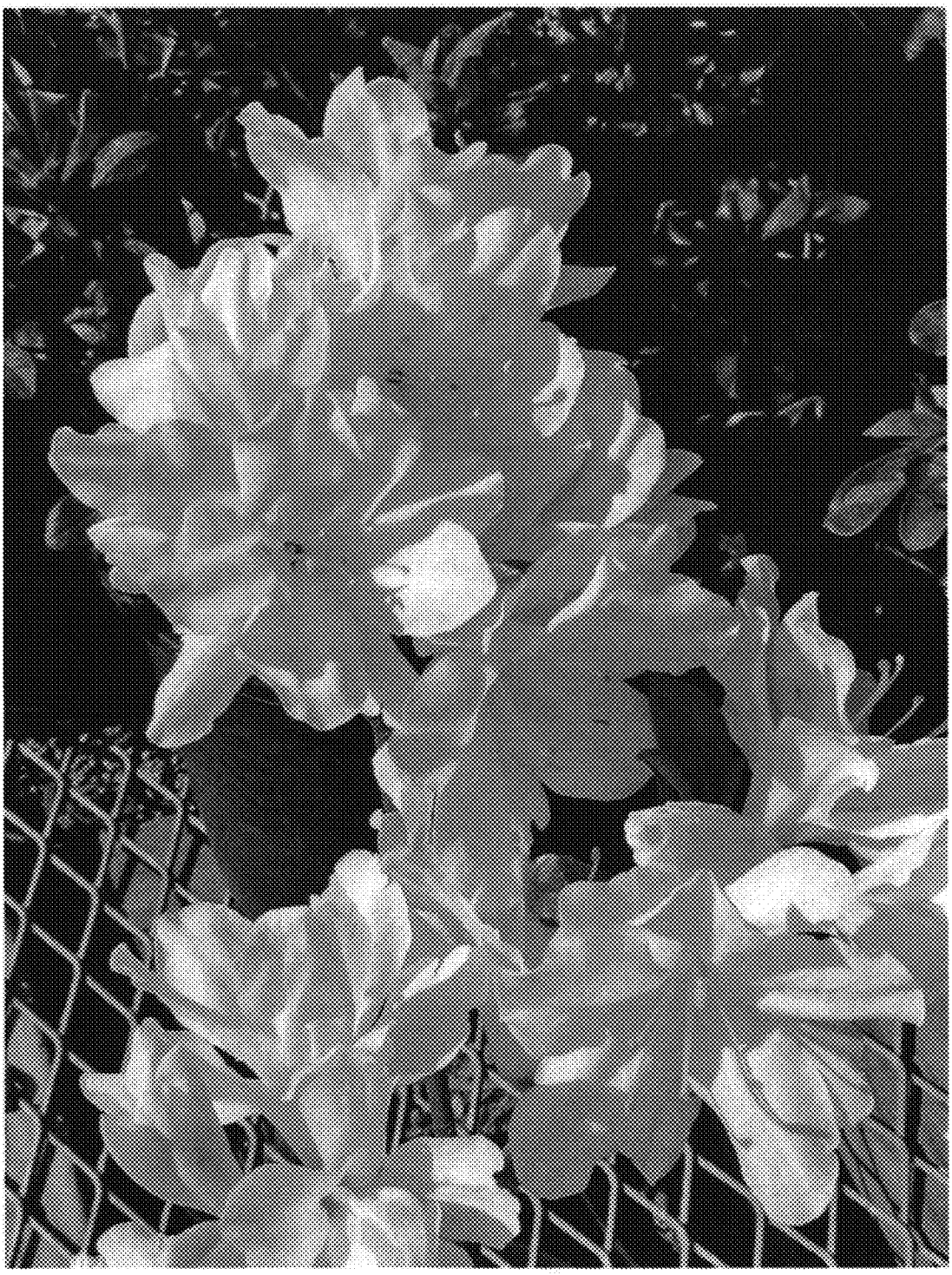

2. The photograph on the FIG. 2 displays a close-up view of typical flowers of 'STEWARD'.

Figure 3:
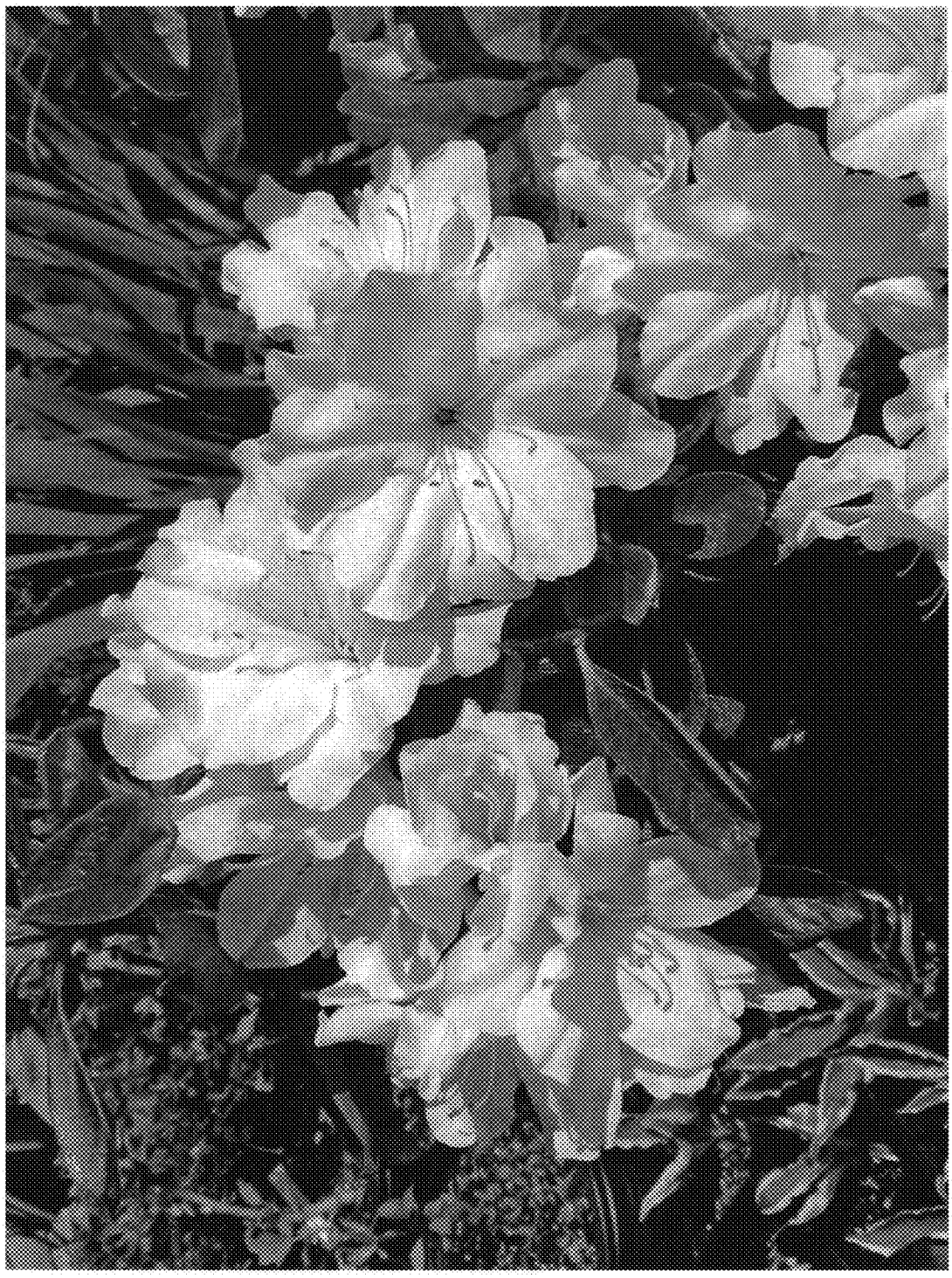

3. The photograph on the FIG. 3 displays a close-up view of typical flowers of 'STEWARD' and includes a view of a typical green-yellow flower bud in the lower righthand area of the photograph.

Colors in the photographs may differ slightly from the color values cited in the detailed botanical description, which accurately describes the colors of the new Azalea.

DETAILED BOTANICAL DESCRIPTION

The following observations, measurements, values, and comparisons are based on observations made of a plant found in an established landscape planting in Charlottesville, Va. between 1975 and 2010 and plants asexually reproduced in commercial production practices at Wooster, Ohio between 1998 and 2010. The plant found in an established landscape planting in Charlottesville, Va. was exposed to temperatures ranging from 39.4° C. in 1977 to −23.3° C. in 1994.

In the following description, color references are made to The Royal Horticultural Society Colour Chart, 1995 Edition, except for color N155A which is from the 2001 Edition and where general terms of ordinary dictionary significance are used.

Botanical classification: *Rhododendron* 'STEWARD'.

Commercial classification: Evergreen ornamental flowering medium shrub for outside landscape planting or for greenhouse-forcing pot azalea.

Parentage:

*Female or seed parent*.—Unknown.

*Male or pollen parent*.—Unknown.

Propagation:

*Type*.—Hardwood, semi-hardwood and softwood vegetative cuttings.

*Time to initiate roots*.—About 4 to 6 weeks.

*Time to develop roots*.—About 6 to 10 weeks.

*Root description*.—Fine, fibrous white.

*Rooting habit*.—Freely spreading and dividing.

Plant description:

*Plant form and growth habit*.—Globe to broad columnar.

*Truss size*.—About 8 inches in diameter.

*Branching habit*.—Freely branching.

*Plant height, soil level to top of flowers*.—About 198 cm.

*Plant diameter, area of spread*.—About 194 cm.

*Lateral branch description*.—Length: About 91 cm. Diameter at base: About 5 mm. Internode length. — About 19.1 mm. Strength: Strong. Texture: Coarse (no difference for young or mature). Color: Young: Close to Green Group 143C. Color: Mature: Close to Green Group 141A.

Foliage description:

*Arrangement*.—Alternate. Foliage retention: Very good. Length: About 5.72 cm. Width: About 2.22 cm. Shape: oval. Apex: mucronate. Base: acuminate. Margin: Entire to slightly toothed. Venation pattern: branched/net. Texture: pubescent underside, very glossy upper side upon maturity on the upper side of the leaves. Color: Young foliage, upper surface: Close to Green Group 143C. Young foliage, lower surface: Close to Green Group 143C. Mature foliage, upper surface: Close to Green Group 141A. Mature foliage, lower surface: Close to Green Group 141C. Petiole: Length: 0" as leaf is sessile. The plant is evergreen and has no fall color.

Flower description:

*Natural flowering season*.—April in Hardiness Zone 5.

*Flower arrangement*.—In a terminal truss defined as a domed cluster of flowers or flower mass.

*Flower fragrance*.—Very slight but sweet.

*Flower appearance*.—Hose-in-hose flower form with a joined whorl of petals in a second whorl of petaloid sepals (transformed sepals), pure white flower with some yellow-green flecking in the throat of the petals. Flowers are 6 to 15 per truss with an average of 10 Flower inflorescence shape is open funnel. Flower shape is conical. Flower throat markings are weak. Flower blooms last about 10 days when grown outside.

*Flower diameter*.—About 3.81 to 5.08 cm

*Flower depth*.—About 3.81 cm.

*Postproduction longevity*.—About 5 to 7 days.

*Flower bud* (*before petal color is showing*).—Buds point outward from a central attachment, are greenish-yellow, and are quite showy even before flowers open.

*Flower bud* (*just starting to show petal color*).—Rate of opening: About 2 days. Length: About 2.54 cm. Diameter: About 9.5 mm. Shape: Oval. Color: Close to Green-Yellow group 1-B.

*Petals*.—Arrangement: Five petals joined in a whorl within the whorl of petaloid sepals. Length: About 2.54 cm. Width: About 12.7 mm. Shape: oval. Margin: entire. Apex: partially ruffled. Base: tapered to its attachment. Texture: both surfaces are glabrous. Color, when opening, upper surface: Close to Green-Yellow Group 154-B to N155A White with slight blotch of Green-Yellow Group 1-C. Color, when opening, lower surface: White (N155A) with throat of close to Green-Yellow Group 1-C. Color, fully opened, upper surface: Clear White (N155A). Color, fully opened, lower surface: Clear White.

*Petaloids*.—Quantity: None.

*Sepals*.—Petal like. Arrangement: Five joined in a whorl. Shape: oval. Margin: Entire. Texture: Glabrous, both surfaces. Color, upper surface: Pure White. Color, lower surface: Pure White (N155A). Sepals are exact duplicates of petals — see [0039] in terms of size and shape.

*Peduncles*.—Length: About 6.35 mm. Diameter: About 1.59 mm. Angle: About 90 degrees. Strength: Strong. Texture: Glabrous. Color: Green (144A).

*Reproductive organs*.—Androecium: Quantity of stamens per flower: Five. Anther size: About 0.79 mm. Anther shape: Oval. Anther color: White (N155A). Filament length: About 3.81 mm. Filament color: White (N155A). Pollen amount: Specifics unknown but judged to be medium. Pollen color: Close to Greyed-Orange Group 163-D. Gynoecium: Pistil quantity: One. Pistil length: Close to 3.18 mm. Stigma shape: Oval. Stigma color: Close to Yellow Group 13-C. Style length: About 3.18 mm. Style color: Green (144A). Ovary color: Green (144A).

*Seed*.—Very fine brown (165A). Number of seeds produced, shape, length and diameter are not available.

Disease/pest resistance: Resistant to most common diseases found on outside azaleas. Slightly susceptible to azalea lace bug.

Drought resistance: Very resistant to drought.

Weather/temperature tolerance: Tolerated temperatures from −23° C. to 39° C. in outside environment.

As compared to the patented 'Tiara' azalea plant described in U.S. Plant Pat. No. 18,948, the azalea plant described herein has a slight smell as noted in paragraph [0032] whereas the 'Tiara' azalea plant is said at column 4 to have no smell. Also the plant of the present invention has hose-in hose flowers as noted in paragraph [0033] and the 'Tiara' azalea plant is said at column 4 to have semi-double to double flowers and the diameter of the flowers in each are much different, 9.75 cm for the 'Tiara' patented azalea plant as noted in column 4 and 3.81 to 5.8 cm for the present invention as described a paragraph [0034]. The azalea plant of the present invention differs from the well known 'Delaware Valley White' commercial cultivar as noted at paragraph [0006]. In a prior application Ser. No. 14/092,552, to which the present invention claims priority the Examiner noted in the Office Action of Nov. 21, 2014 that the prior art 'Shammarello' patent U.S. Plant Pat. No. 2,508 has only three flowers borne in the terminal truss while the instant invention has an average of 10 and also the prior art azalea does not produce fragrant flowers while the present invention does have a slight smell.

It is claimed:

1. A new and distinct Azalea plant, substantially as illustrated and described herein.

* * * * *